(12) United States Patent
Wei et al.

(10) Patent No.: US 9,671,460 B2
(45) Date of Patent: Jun. 6, 2017

(54) DETECTING APPARATUS AND DETECTING METHOD

(71) Applicants: BOE TECHNOLOGY GROUP CO., LTD., Beijing (CN); HEFEI XINSHENG OPTOELECTRONICS TECHNOLOGY CO., LTD., Anhui (CN)

(72) Inventors: Chuanbing Wei, Beijing (CN); Xiaoming Zhang, Beijing (CN); Song Wu, Beijing (CN)

(73) Assignees: BOE TECHNOLOGY GROUP CO., LTD., Beijing (CN); HEFEI XINSHENG OPTOELECTRONICS TECHNOLOGY CO., LTD., Hefei, Anhui (CN)

( * ) Notice: Subject to any disclaimer, the term of this patent is extended or adjusted under 35 U.S.C. 154(b) by 27 days.

(21) Appl. No.: 14/744,576

(22) Filed: Jun. 19, 2015

(65) Prior Publication Data

US 2016/0161555 A1    Jun. 9, 2016

(30) Foreign Application Priority Data

Dec. 4, 2014 (CN) .......................... 2014 1 0735273

(51) Int. Cl.
*G01N 21/00* (2006.01)
*G01R 31/308* (2006.01)
(Continued)

(52) U.S. Cl.
CPC ....... *G01R 31/308* (2013.01); *G01N 21/8851* (2013.01); *G01N 21/95* (2013.01); *G01N 2021/9513* (2013.01)

(58) Field of Classification Search
CPC ....... G01N 2021/9513; G01N 21/8851; G01N 21/95; G01R 31/308
(Continued)

(56) References Cited

U.S. PATENT DOCUMENTS

| 2010/0013505 A1* | 1/2010 | Takekoshi .......... G01R 31/2887 324/754.21 |
| 2011/0310244 A1* | 12/2011 | Schweitzer .......... G01N 21/896 348/92 |

FOREIGN PATENT DOCUMENTS

| CN | 101672804 A | 3/2010 |
| CN | 101819165 A | 9/2010 |

(Continued)

OTHER PUBLICATIONS

Notification of the First Office Action dated Jun. 20, 2016 corresponding to Chinese application No. 201410735273.0.

(Continued)

*Primary Examiner* — Tri T Ton
(74) *Attorney, Agent, or Firm* — Nath, Goldberg & Meyer; Joshua B. Goldberg; Christopher Thomas

(57) ABSTRACT

The present invention provides a detecting apparatus and a detecting method. The detecting apparatus comprises: a base, a light source module, an image generating unit and a detecting unit. The light source module is configured to generate detecting light and cause the detecting light to irradiate towards the image generating unit after passing through an area of a shorting bar circuit in a panel. The image generating unit is configured to receive the detecting light irradiating thereon, and generate a detecting image of the area of the shorting bar circuit. The detecting unit is configured to detect whether the shorting bar circuit in the panel is cut off based on the detecting image. As the detecting light passing through the panel lasts for a longer (Continued)

time and is of higher brightness, the detecting image generated by the image generating unit is clearer.

<div align="center">19 Claims, 5 Drawing Sheets</div>

(51) Int. Cl.
    *G01N 21/88*     (2006.01)
    *G01N 21/95*     (2006.01)

(58) Field of Classification Search
    USPC ..................... 356/237.1–237.6, 239.1–239.8
    See application file for complete search history.

(56)               References Cited

<div align="center">FOREIGN PATENT DOCUMENTS</div>

| | | |
|---|---|---|
| CN | 101988908 A | 3/2011 |
| CN | 1023849x8 A | 3/2012 |
| CN | 102621149 A | 8/2012 |
| CN | 103868925 A | 6/2014 |

<div align="center">OTHER PUBLICATIONS</div>

Notification of the Second Office Action dated Feb. 16, 2017 corresponding to Chinese application No. 201410735273.0.

* cited by examiner

DETECTING APPARATUS AND DETECTING METHOD

FIELD OF THE INVENTION

The present invention relates to the field of display technology, and particularly relates to a detecting apparatus and a detecting method.

BACKGROUND OF THE INVENTION

Currently, in the fabrication of a panel, an electrical detection needs to be performed on a display substrate or the assembled panel before bonding a driving chip, that is, a signal detecting device inputs a signal into the panel through a terminal of a signal line of the panel, so as to detect whether a defect exists in the panel.

In the process of performing the electric detection, a shorting bar is generally used to lead a signal line to a relatively spacious region, and a detecting probe is connected to a terminal of the shorting bar. Since intervals between terminals of the shorting bars may be relatively large, demand on accuracy of the detecting probes is relatively low. After the electric detection is finished, the shorting bar circuits need to be cut off or removed by way of laser cutting, and meanwhile, it is necessary to use a corresponding detecting apparatus to detect the areas of the shorting bar circuits, so as to ensure that the shorting bar circuits in the panel are completely cut off.

FIG. 1 is a schematic diagram of a structure of a detecting apparatus in the prior art, and FIG. 2 is a schematic diagram of a detecting image generated by an image generating unit in the detecting apparatus shown in FIG. 1. As shown in FIGS. 1 and 2, the detecting apparatus comprises: a base 3, an image generating unit 6 (which is generally a camera) and a detecting unit 7. Positioning pillars 4 for supporting a lower surface of a panel 1 and positioning the panel 1 are provided on the base 3. The image generating unit 6 is arranged above the panel 1, and is connected to the detecting unit 7. The detecting process of the detecting apparatus is as follows. At first, the image generating unit 6 emits detecting light 5, which lasts for a relatively short time, onto the area of a shorting bar circuit 2 on the panel, at this point, the shorting bar circuit 2 remaining on the panel will reflect the detecting light 5 to the image generating unit 6, while for the area of the panel where no shorting bar circuit 2 remains, the detecting light 5 will be transmitted to the base 3 directly and absorbed by the base 3. Then, the image generating unit 6 generates a detecting image of the area of the shorting bar circuit 2 on the panel according to the received reflected detecting light 5, and in the detecting image, it is white at a position corresponding to a part of the panel where the shorting bar circuit 2 remains, and it is back at a position corresponding to a part of the panel where no shorting bar circuit 2 remains. At last, the detecting unit 7 can determine whether the shorting bar circuit 2 is cut off based on the detecting image. Specifically, when it is black at a position that corresponds to a laser cutting area 20 in the detecting image, it can be determined that the shorting bar circuit 2 is cut off.

However, in a practical detecting process, since the detecting light emitted from the image generating unit 6 lasts for a short time and is of low brightness, and meanwhile wires in the shorting bar circuit 2 are relatively thin, the effect of reflecting of the detecting light 5 by the shorting bar circuit 2 is not good, and therefore, the detecting image generated by the image generating unit 6 cannot reflect the actual situation of the shorting bar circuit 2 accurately. For example, in a situation in which some shorting bar circuits 2 are not cut off in the laser cutting areas 20, but a part of the detecting image corresponding to the shorting bar circuit 2 that is not cut off is black due to bad reflecting effect by the shorting bar circuit 2, when the detecting unit 7 judges based on the detecting image, it will be determined that no shorting bar circuit 2 remains in the area, that is, it is mistakenly detected that the shorting bar circuit 2 is cut off, thus resulting in missed detection.

SUMMARY OF THE INVENTION

An object of the present invention is to provide a detecting apparatus and a detecting method, which can detect more accurately whether a shorting bar circuit in a panel is cut off.

According to an aspect of the present invention, there is provided a detecting apparatus, which is configured to detect whether a shorting bar circuit in a panel is cut off, and the detecting apparatus comprises: a base, a light source module, an image generating unit and a detecting unit, wherein, the light source module is configured to generate detecting light and cause the detecting light to irradiate towards the image generating unit after passing through the area of the shorting bar circuit in the panel;

the image generating unit is configured to receive the detecting light irradiating thereon, and generate a detecting image of the area of the shorting bar circuit; and the detecting unit is configured to detect whether the shorting bar circuit in the panel is cut off based on the detecting image.

In an example, positioning pillars for supporting a lower surface of the panel and positioning the panel are provided on the base, and the image generating unit is arranged above the panel.

In an example, the light source module comprises: a first surface light source arranged above the panel and a reflecting mechanism arranged below the panel, wherein, the first surface light source is configured to generate the detecting light, the detecting light generated by the first surface light source irradiates towards the reflecting mechanism after sequentially passing through an upper surface and the lower surface of the panel; and the reflecting mechanism is configured to reflect, to the area of the shorting bar circuit in the panel, the detecting light exiting from the lower surface of the panel, so that the detecting light reflected by the reflecting mechanism irradiates towards the image generating unit after sequentially passing through the lower surface and the upper surface of the panel.

In an example, the reflecting mechanism comprises: a reflecting film, which is provided on the base.

In an example, the reflecting film is an aluminum film.

In an example, the reflecting mechanism comprises: a reflecting mirror and a first adjusting unit, wherein the first adjusting unit is provided on the base and connected to the reflecting mirror, and is configured to adjust a reflecting direction of the reflecting mirror.

In an example, the reflecting mirror is a plane mirror, a concave reflecting mirror or a total reflecting prism.

In an example, the light source module further comprises a second adjusting unit provided on the image generating unit and connected to the first surface light source, and the second adjusting unit is configured to adjust an irradiating direction of the detecting light generated by the first surface light source.

In an example, the light source module comprises: a second surface light source provided on the base, the second surface light source is configured to generate the detecting light, and the detecting light generated by the second surface light source irradiates towards the image generating unit after sequentially passing through the lower surface of the panel and the upper surface of the panel.

In an example, the light source module comprises: a third surface light source provided below the base, and the base is a transparent base, wherein, the third surface light source is configured to generate the detecting light, and the detecting light generated by the third surface light source irradiates towards the image generating unit after sequentially passing through the base, the lower surface of the panel and the upper surface of the panel.

In an example, the detecting unit comprises: a color determining module configured to determine whether it is white at a position in the detecting image corresponding to a laser cutting area, if the color determining module determines that it is white at the position in the detecting image corresponding to the laser cutting area, it is detected that the shorting bar circuit is cut off, if the color determining module determines that it is black at the position in the detecting image corresponding to the laser cutting area, it is detected that the shorting bar circuit is not cut off.

In an example, the color determining module comprises: a grayscale calculation sub-module and a grayscale comparison sub-module which are connected to each other, wherein, the grayscale calculation sub-module is configured to calculate a grayscale value at the position in the detecting image corresponding to the laser cutting area; and the grayscale comparison sub-module is configured to determine whether the grayscale value is larger than a reference grayscale value, if the grayscale value is smaller than or equal to the reference grayscale value, it is determined that it is white at the position in the detecting image corresponding to the laser cutting area, if the grayscale value is larger than the reference grayscale value, it is determined that it is black at the position in the detecting image corresponding to the laser cutting area.

According to another aspect of the present invention, there is provided a detecting method for detecting whether a shorting bar circuit in a panel is cut off, the detecting method is based on a detecting apparatus, which comprises: a base, a light source module, an image generating unit and a detecting unit, and the detecting method comprises steps of:

generating, by the light source module, detecting light, and causing the detecting light to irradiate towards the image generating unit after passing through the area of the shorting bar circuit in the panel;

receiving the detecting light irradiating thereon and generating a detecting image of the area of the shorting bar circuit, by the image generating unit; and detecting, by the detecting unit, whether the shorting bar circuit in the panel is cut off based on the detecting image.

The present invention has the beneficial effects as follows.

The present invention provides a detecting apparatus and a detecting method, and the detecting apparatus comprises: a base, a light source module, an image generating unit and a detecting unit. In the technical solutions of the present invention, the light source module generates detecting light and causes the detecting light to irradiate towards the image generating unit after passing through the area of the shorting bar circuit in the panel (i.e., passing through the panel), and the image generating unit then generates a detecting image. As the detecting light passing through the area of the shorting bar circuit in the panel lasts for a relatively long time and is of relatively high brightness, the detecting image generated by the image generating unit is relatively clear, that is, the detecting image can reflect the actual situation of the shorting bar circuit more clearly and accurately. In this case, the detecting unit can detect more accurately whether the shorting bar circuit in the panel is cut off based on the detecting image.

DETAILED DESCRIPTION OF THE EMBODIMENTS

To make those skilled in the art better understand the technical solutions of the present invention, a detecting apparatus and a detecting method provided by the present invention will be described in detail below in combination with the accompanying drawings.

Figure 1:
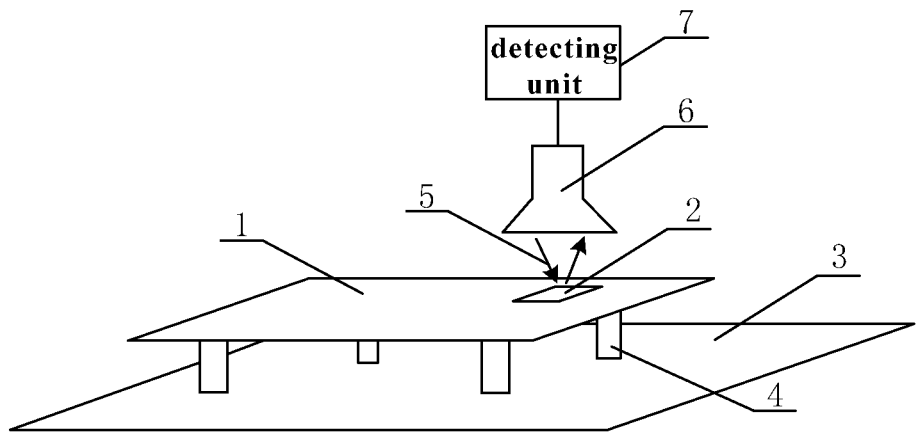
FIG. 1 is a schematic diagram of a structure of a detecting apparatus in the prior art.
Figure 2:
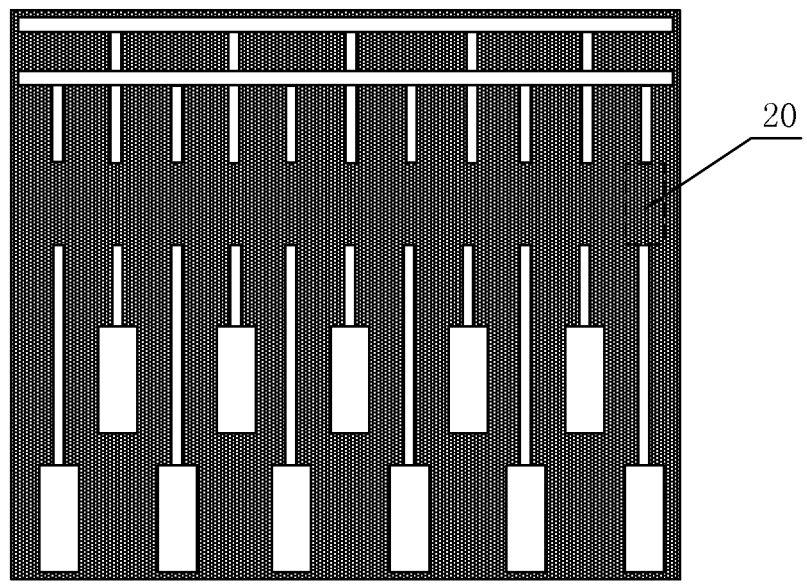
FIG. 2 is a schematic diagram of a detecting image generated by the image generating unit in the detecting apparatus shown in FIG. 1.
Figure 3:
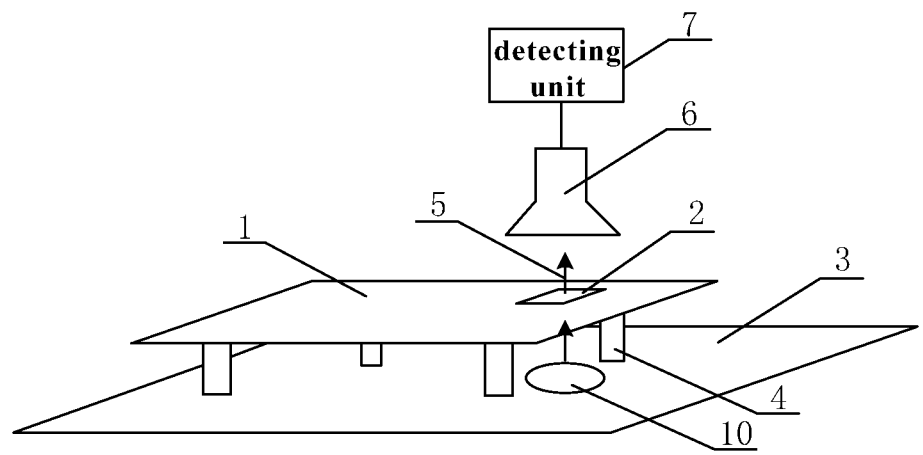
FIG. 3 is a schematic diagram of a structure of a detecting apparatus provided by Embodiment 1 of the present invention.
Figure 4:
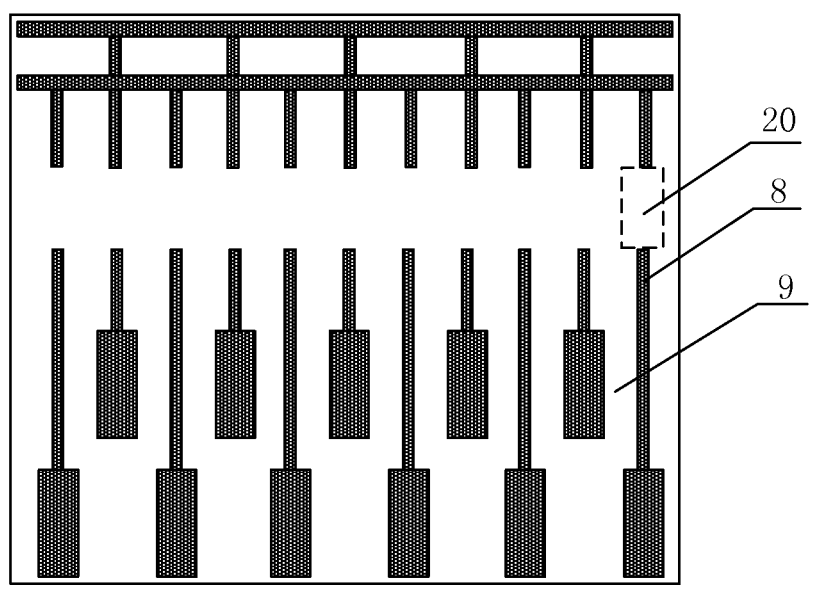
FIG. 4 is a schematic diagram of a detecting image generated by the image generating unit in the detecting apparatus shown in FIG. 3.

FIG. 3 is a schematic diagram of a structure of a detecting apparatus provided by Embodiment 1 of the present invention, and FIG. 4 is a schematic diagram of a detecting image generated by the image generating unit in the detecting apparatus shown in FIG. 3. As shown in FIGS. 3 and 4, the detecting apparatus is configured to detect whether a shorting bar circuit 2 in a panel 1 is cut off, and the detecting apparatus comprises: a base 3, a light source module, an image generating unit 6 and a detecting unit 7. Positioning pillars 4 for supporting a lower surface of the panel 1 and positioning the panel 1 are provided on the base 3, and the image generating unit 6 is arranged above the panel 1 and connected to the detecting unit 7. The light source module is configured to generate detecting light 5 and cause the detecting light 5 to irradiate towards the image generating unit 6 after passing through the area of the shorting bar circuit 2 in the panel 1. In the present embodiment, the light source module comprises a second surface light source 10 provided on the base 3, and the detecting light 5 generated by the second surface light source 10 irradiates towards the image generating unit 6 after passing through the area of the shorting bar circuit 2 in the panel 1. Specifically, the detecting light 5 irradiates towards the upper surface of the panel 1 from the lower surface of the panel 1, and thus passing through the area of the shorting bar circuit 2 in the panel 1. It should be noted that, the second surface light source 10 may comprises a plurality of LED lamps. The image generating unit 6 is configured to receive the detecting light 5 irradiating thereon (i.e, the detecting light 5 transmitted out from the upper surface of the panel 1), and generate a detecting image of the area of the shorting bar circuit 2. The detecting unit 7 is configured to detect whether the shorting bar circuit 2 in the panel 1 is cut off based on the detecting image.

The working principle of the detecting apparatus provided by the present embodiment is as follow.

At first, the light source module generates detecting light 5, and causes the detecting light 5 to irradiate towards the image generating unit 6 after passing through the area of the shorting bar circuit 2 in the panel 1. At this point, at a part of the area of the shorting bar circuit 2 where a part of the shorting bar circuit 2 remains, the detecting light 5 will be blocked by the part of the shorting bar circuit 2, while at a part of the area of the shorting bar circuit 2 where no shorting bar circuit 2 remains, the detecting light 5 will be transmitted into the image generating unit 6.

Then, the image generating unit 6 generates a detecting image of the area of the shorting bar circuit 2 in the panel 1 based on the received transmitted detecting light 5. In the detecting image, it is black at a position 8 corresponding to a part of the panel 1 where the shorting bar circuit 2 remains, while it is white at a position 9 (and position 20) corresponding to a part of the panel 1 where no shorting bar circuit 2 remains.

At last, the detecting unit 7 can detect whether the shorting bar circuit 2 is cut off according to the detecting image.

Figure 5:
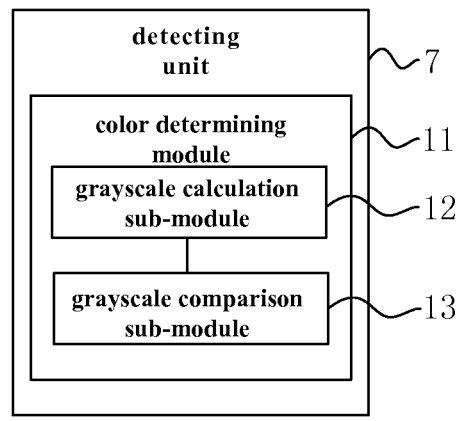
FIG. 5 is a block diagram of a structure of a detecting unit in a detecting apparatus provided by the present invention.

FIG. 5 is a block diagram of a structure of a detecting unit 7 in a detecting apparatus provided by the present invention. As shown in FIG. 5, the detecting unit 7 may comprise: a color determining module 11 configured to determine whether it is white at a position in the detecting image corresponding to a laser cutting area 20, if it is white at the position in the detecting image corresponding to the laser cutting area 20, it is determined that the shorting bar circuit 2 is cut off, if it is black at the position in the detecting image corresponding to the laser cutting area 20, it is determined that the shorting bar circuit 2 is not cut off. Further, the color determining module 11 may comprise: a grayscale calculation sub-module 12 and a grayscale comparison sub-module 13 which are connected to each other. The grayscale calculation sub-module 12 is configured to calculate a grayscale value at the position in the detecting image corresponding to the laser cutting area 20, and the grayscale comparison sub-module 13 is configured to determine whether the grayscale value is larger than a reference grayscale value, if the grayscale comparison sub-module 13 determines that the grayscale value is smaller than or equal to the reference grayscale value, it is determined that it is white at the position in the detecting image corresponding to the laser cutting area 20, if the grayscale comparison sub-module 13 determines that the grayscale value is larger than the reference grayscale value, it is determined that it is black at the position in the detecting image corresponding to the laser cutting area 20.

It should be additionally noted that, in the present embodiment, the base 3 may be covered by LEDs lamps, so as to meet requirements of detections of panels 1 with different sizes and shorting bar circuits 2 at different positions of the panel 1.

Compared to the prior art, the detecting apparatus provided by the present embodiment comprises the light source module, the detecting light 5 generated by the light source module irradiates towards the image generating unit 6 after passing through the area of the shorting bar circuit 2 in the panel 1 (i.e., passing through the panel 1), and the image generating unit 6 then generates a detecting image. As the detecting light 5 passing through the area of the shorting bar circuit 2 in the panel 1 lasts for a relatively long time and is of relatively high brightness, the detecting image generated by the image generating unit 6 is relatively clear, that is, the generated detecting image can reflect the actual situation of the shorting bar circuit 2 more clearly and accurately. In this case, the detecting result obtained by the detecting unit 7 based on the detecting image will be relatively accurate.

Figure 6:
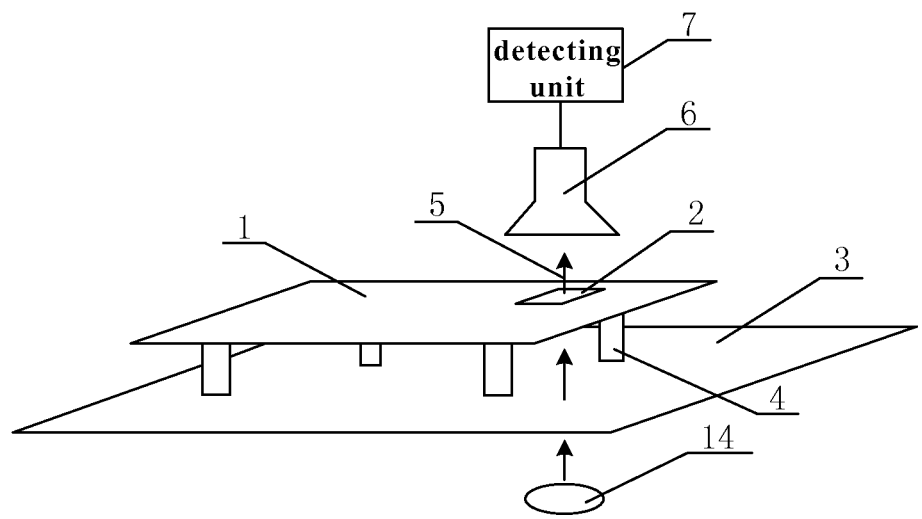
FIG. 6 is a schematic diagram of a structure of a detecting apparatus provided by Embodiment 2 of the present invention.

FIG. 6 is a schematic diagram of a structure of a detecting apparatus provided by Embodiment 2 of the present invention. As shown in FIG. 6, the present embodiment differs from the above Embodiment 1 in that, the light source module in the present embodiment comprises: a third surface light source 14 provided below the base 3, and the base 3 is a transparent base. The third surface light source 14 is configured to generate detecting light 5, and the detecting light 5 generated by the third surface light source 14 irradiates towards the image generating unit 6 after sequentially passing through the base 3, the lower surface and the upper surface of the panel 1.

In the present embodiment, the third surface light source 14 may comprise a plurality of LED lamps and a supporting plate for supporting the LED lamps.

Compared with the above Embodiment 1, the third surface light source 14 in the present embodiment is provided below the base 3, and the base 3 is provided as a transparent base 3, which can effectively avoid damage caused by contact between the third surface light source 14 and other device(s), thus effectively prolonging lifespan of the third surface light source 14.

Figure 7:
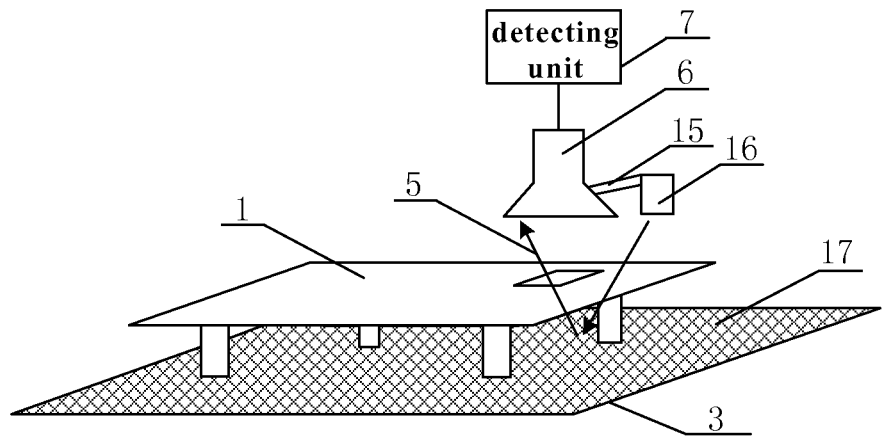
FIG. 7 is a schematic diagram of a structure of a detecting apparatus provided by Embodiment 3 of the present invention.

FIG. 7 is a schematic diagram of a structure of a detecting apparatus provided by Embodiment 3 of the present invention. As shown in FIG. 7, the present embodiment differs from the above Embodiment 1 and Embodiment 2 in that, the light source module in the present embodiment comprises: a first surface light source 16 provided above the panel 1 and a reflecting mechanism provided below the panel 1. The first surface light source 16 is configured to generate detecting light 5, the detecting light 5 generated by the first surface light source 16 irradiates towards the reflecting mechanism after passing through the panel 1 (specifically, sequentially passing through the upper surface and the lower surface of the panel 1), and the reflecting mechanism is configured to reflect, to the area of the shorting bar circuit 2 in the panel 1, the detecting light 5 irradiating thereon (i.e., the detecting light 5 exiting from the lower surface of the panel 1), so that the detecting light 5 reflected by the reflecting mechanism irradiates towards the image generating unit 6 after passing through the area of the shorting bar circuit 2 in the panel 1 (i.e., sequentially passing through the lower surface and the upper surface of the panel 1). The first surface light source 16 may comprises a plurality of LED lamps.

In the present embodiment, the reflecting mechanism is a layer of reflecting film 17, and the reflecting film 17 is provided on the base 3. Specifically, the reflecting film 17 may be an aluminum film.

In practical manufacturing process, laser cutting of the shorting bar circuit 2 and detection of the cutting effect are performed on the same base 3, while in the process of laser cutting, a part of laser may penetrate the panel 1 and irradiate onto the base 3. Therefore, if an electric device (e.g., the second surface light source 10 in the above Embodiment 1 or the third surface light source 14 in the above Embodiment 2) is provided below the panel 1, the electric device can be easily damaged in the process of laser cutting.

In the present embodiment, by providing the first surface light source 16 above the panel 1 and covering the base 3 with one layer of reflecting film 17, the detecting light 5 can irradiate towards the image generating unit 6 after passing through the area of the shorting bar circuit 2 in the panel 1, without providing an electric device below the panel 1, and thus the above technical problem is effectively solved.

To facilitate adjusting irradiating direction of the detecting light 5, the light source module may further comprises a second adjusting unit 15. The second adjusting unit 15 is provided on the image generating unit 6 and connected to the first surface light source 16, and the second adjusting unit 15 is configured to adjust an irradiating direction of the detecting light 5 generated by the first surface light source 16. With the second adjusting unit 15, the detecting light 5 reflected by the reflecting film 17 can be easily controlled to irradiate towards the area of the shorting bar circuit 2 on the panel 1.

Figure 8:
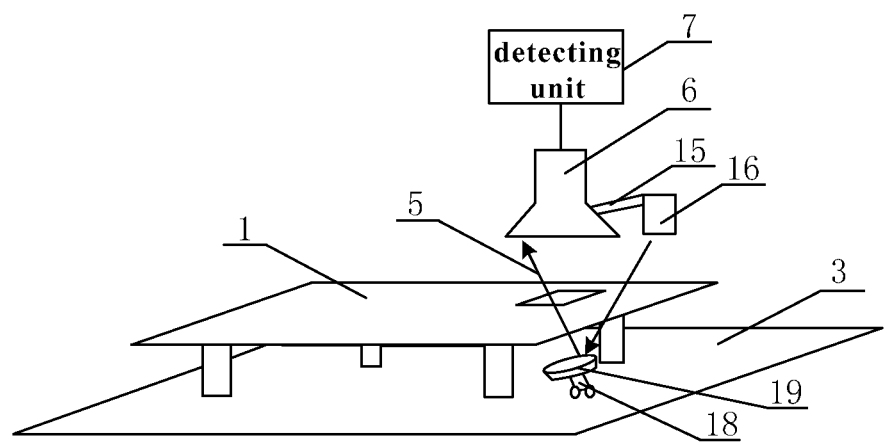
FIG. 8 is a schematic diagram of a structure of a detecting apparatus provided by Embodiment 4 of the present invention.

FIG. 8 is a schematic diagram of a structure of a detecting apparatus provided by Embodiment 4 of the present invention. As shown in FIG. 8, the present embodiment differs from the above Embodiment 3 in that, the light source module in the present embodiment comprises: a first surface light source 16, a reflecting mirror 19 and a first adjusting unit 18. The first adjusting unit 18 is provided on the base 3 and connected to the reflecting mirror 19, and the first adjusting unit 18 is configured to adjust a reflecting direction of the reflecting mirror 19.

In the present invention, the second adjusting unit 15 is configured to adjust the irradiating direction of the detecting light 5 generated by the first surface light source 16, so that the detecting light 5 irradiates towards the reflecting mirror 19. The first adjusting unit 18 is configured to adjust the reflecting direction of the reflecting mirror 19, so that the detecting light 5 reflected by the reflecting mirror 19 irradiates towards the area of the shorting bar circuit 2 on the panel 1.

In the present embodiment, the reflecting mirror 19 may be a plane mirror, a concave reflecting mirror or a total reflecting prism. When the reflecting mirror 19 is a concave reflecting mirror, the detecting light 5 can be converged. In this case, the detecting light 5 reflected to the area of the shorting bar circuit 2 by the concave reflecting mirror can have enhanced brightness, accordingly, the detecting image generated by the image generating unit 6 can be clearer, and thus accuracy of the detecting result can be effectively improved.

It should be noted that, the detecting image generated by the image generating unit 6 in the detecting apparatus provided by any one of the above Embodiments 2 to 4 may refer to that shown in FIG. 4, and detailed description thereof is omitted herein.

It should be noted that, in any one of the detecting apparatuses in the above Embodiments 1 to 4, the positions, in the vertical direction, of the image generating unit 6, the detecting unit 7 and the light source module with respect to the panel 1 may be changed, as long as the detecting light 5 emitted from the light source module can irradiate towards the image generating unit 6 after passing through the area of the shorting bar circuit 2 in the panel 1. For example, in FIG. 6, the image generating unit 6 may be provided below the panel 1 (or below the transparent base 3), and the third surface light source 14 may be provided above the panel 1.

The detecting apparatus provided by the embodiments of the present invention comprises: a base, a light source module, an image generating unit and a detecting unit. In the technical solution of the present invention, the light source module generates detecting light and causes the detecting light to irradiate towards the image generating unit after passing through the area of the shorting bar circuit in the panel, and the image generating unit then generates a detecting image. As the detecting light passing through the area of the shorting bar circuit in the panel lasts for a relatively long time and is of relatively high brightness, the detecting image generated by the image generating unit is relatively clear, that is, the detecting image can reflect the actual situation of the shorting bar circuit more clearly and accurately. In this case, the detecting unit can detect more accurately whether the shorting bar circuit in the panel is cut off based on the detecting image.

Figure 9:
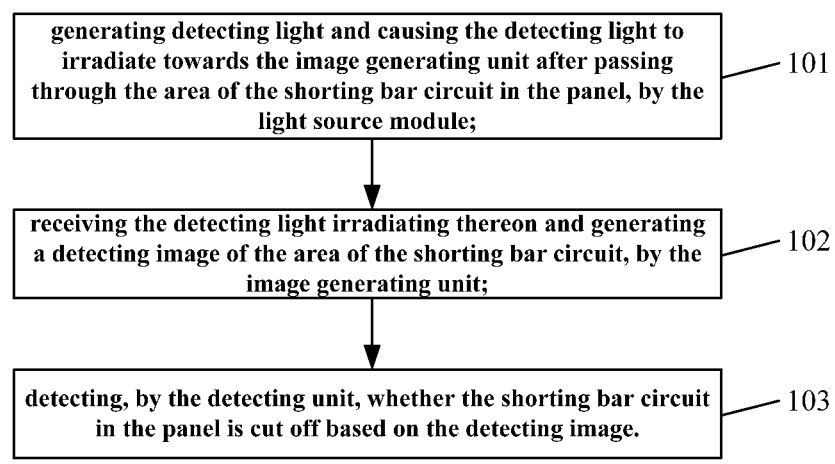
FIG. 9 is a flowchart of a detecting method provided by Embodiment 5 of the present invention.

FIG. 9 is a flowchart of a detecting method provided by Embodiment 5 of the present invention. As shown in FIG. 9, the detecting method is used for detecting whether a shorting bar circuit in a panel is cut off, and the detecting method is based on a detecting apparatus, which comprises: a base, a light source module, an image generating unit and a detecting unit, and the detecting method comprises:

step 101: generating detecting light and causing the detecting light to irradiate towards the image generating unit after passing through the area of the shorting bar circuit in the panel, by the light source module;

step 102: receiving the detecting light irradiating thereon and generating a detecting image of the area of the shorting bar circuit, by the image generating unit; and step 103: detecting, by the detecting unit, whether the shorting bar circuit in the panel is cut off based on the detecting image.

It can be understood that, in the step 101, the light source module may be the light source module provided by any one of Embodiments 1 to 4. Specific description of the light source module may refer to the description of each of the above embodiments, and is not repeated herein. In the steps 102 and 103, operations of the image generating unit and the detecting unit may refer to the description in Embodiment 1, and are not repeated herein.

In the detecting method provided by the present embodiment, detecting light is generated by the light source module and the detecting light is caused to irradiate towards the image generating unit after passing through the area of the shorting bar circuit in the panel, and a detecting image is then generated by the image generating unit. As the detecting light passing through the area of the shorting bar circuit in the panel lasts for a relatively long time and is of relatively high brightness, the detecting image generated by the image generating unit is relatively clear, that is, the detecting image can reflect the actual situation of the shorting bar circuit more clearly and accurately. In this case, the detecting unit can detect more accurately whether the shorting bar circuit in the panel is cut off based on the detecting image.

It could be understood that, the above embodiments are merely exemplary embodiments adopted for describing the principle of the present invention, but the present invention is not limited thereto. Various modifications and improvements may be made without departing from the spirit and essence of the present invention, and these modifications and improvements are regarded as within the protection scope of the present invention.

The invention claimed is:

1. A detecting apparatus, configured to detect whether a shorting bar circuit in a panel is cut off, comprising: a base, a light source module, an image generating unit and a detecting unit, wherein,
the light source module is configured to generate detecting light and cause the detecting light to irradiate towards the image generating unit after passing through an area of the shorting bar circuit in the panel;
the image generating unit is configured to receive the detecting light irradiating thereon, and generate a detecting image of the area of the shorting bar circuit; and
the detecting unit is configured to detect whether the shorting bar circuit in the panel is cut off based on the detecting image.

2. The detecting apparatus according to claim 1, wherein, the base is provided thereon with positioning pillars for supporting a lower surface of the panel and positioning the panel, and the image generating unit is arranged above the panel.

3. The detecting apparatus according to claim 2, wherein, the light source module comprises: a first surface light source arranged above the panel and a reflecting mechanism arranged below the panel,
the first surface light source is configured to generate the detecting light, the detecting light generated by the first surface light source irradiates towards the reflecting mechanism after sequentially passing through an upper surface and the lower surface of the panel; and
the reflecting mechanism is configured to reflect, to the area of the shorting bar circuit in the panel, the detecting light exiting from the lower surface of the panel, so that the detecting light reflected by the reflecting mechanism irradiates towards the image generating unit after sequentially passing through the lower surface and the upper surface of the panel.

4. The detecting apparatus according to claim 3, wherein, the reflecting mechanism comprises: a reflecting film, which is provided on the base.

5. The detecting apparatus according to claim 4, wherein, the reflecting film is an aluminum film.

6. The detecting apparatus according to claim 3, wherein, the reflecting mechanism comprises: a reflecting mirror and a first adjusting unit,
the first adjusting unit is provided on the base and connected to the reflecting mirror, and is configured to adjust a reflecting direction of the reflecting mirror.

7. The detecting apparatus according to claim 6, wherein, the reflecting mirror is a plane mirror, a concave reflecting mirror or a total reflecting prism.

8. The detecting apparatus according to claim 3, wherein, the light source module further comprises: a second adjusting unit provided on the image generating unit and connected to the first surface light source, and the second adjusting unit is configured to adjust an irradiating direction of the detecting light generated by the first surface light source.

9. The detecting apparatus according to claim 4, wherein, the light source module further comprises: a second adjusting unit provided on the image generating unit and connected to the first surface light source, and the second adjusting unit is configured to adjust an irradiating direction of the detecting light generated by the first surface light source.

10. The detecting apparatus according to claim 5, wherein, the light source module further comprises: a second adjusting unit provided on the image generating unit and connected to the first surface light source, and the second adjusting unit is configured to adjust an irradiating direction of the detecting light generated by the first surface light source.

11. The detecting apparatus according to claim 6, wherein, the light source module further comprises: a second adjusting unit provided on the image generating unit and connected to the first surface light source, and the second adjusting unit is configured to adjust an irradiating direction of the detecting light generated by the first surface light source.

12. The detecting apparatus according to claim 7, wherein, the light source module further comprises: a second adjusting unit provided on the image generating unit and connected to the first surface light source, and the second adjusting unit is configured to adjust an irradiating direction of the detecting light generated by the first surface light source.

13. The detecting apparatus according to claim 2, wherein, the light source module comprises: a second surface light source provided on the base, the second surface light source is configured to generate the detecting light, and the detecting light generated by the second surface light source irradiates towards the image generating unit after sequentially passing through the lower surface of the panel and an upper surface of the panel.

14. The detecting apparatus according to claim 2, wherein, the light source module comprises: a third surface light source provided below the base, and the base is a transparent base, wherein,
the third surface light source is configured to generate the detecting light, and the detecting light generated by the third surface light source irradiates towards the image generating unit after sequentially passing through the base, the lower surface of the panel and an upper surface of the panel.

15. The detecting apparatus according to claim 1, wherein, the detecting unit comprises: a color determining module, which is configured to determine whether it is white at a position in the detecting image corresponding to a laser cutting area, if the color determining module determines that it is white at the position in the detecting image corresponding to the laser cutting area, it is detected that the shorting bar circuit is cut off; if the color determining module determines that it is black at the position in the detecting image corresponding to the laser cutting area, it is detected that the shorting bar circuit is not cut off.

16. The detecting apparatus according to claim 2, wherein, the detecting unit comprises: a color determining module, which is configured to determine whether it is white at a position in the detecting image corresponding to a laser cutting area, if the color determining module determines that it is white at the position in the detecting image corresponding to the laser cutting area, it is detected that the shorting bar circuit is cut off; if the color determining module determines that it is black at the position in the detecting image corresponding to the laser cutting area, it is detected that the shorting bar circuit is not cut off.

17. The detecting apparatus according to claim 15, wherein, the color determining module comprises: a grayscale calculation sub-module and a grayscale comparison sub-module which are connected to each other, wherein, the grayscale calculation sub-module is configured to calculate a grayscale value at the position in the detecting image corresponding to the laser cutting area; and the grayscale comparison sub-module is configured to determine whether the grayscale value is larger than a reference grayscale value, if the grayscale value is smaller than or equal to the reference grayscale value, it is determined that it is white at the position in the detecting image corresponding to the laser cutting area, if the grayscale value is larger than the reference grayscale value, it is determined that it is black at the position in the detecting image corresponding to the laser cutting area.

18. The detecting apparatus according to claim 16, wherein, the color determining module comprises: a grayscale calculation sub-module and a grayscale comparison sub-module which are connected to each other, wherein, the grayscale calculation sub-module is configured to calculate a grayscale value at the position in the detecting image corresponding to the laser cutting area; and the grayscale comparison sub-module is configured to determine whether the grayscale value is larger than a reference grayscale value, if the grayscale value is smaller than or equal to the reference grayscale value, it is determined that it is white at the position in the detecting image corresponding to the laser cutting area, if the grayscale value is larger than the reference grayscale value, it is determined that it is black at the position in the detecting image corresponding to the laser cutting area.

19. A detecting method, used for detecting whether a shorting bar circuit in a panel is cut off, wherein the detecting method is based on a detecting apparatus, which comprises: a base, a light source module, an image generating unit and a detecting unit, and the detecting method comprises steps of:

generating, by the light source module, detecting light, and causing the detecting light to irradiate towards the image generating unit after passing through an area of the shorting bar circuit in the panel;

receiving the detecting light irradiating thereon and generating a detecting image of the area of the shorting bar circuit, by the image generating unit; and detecting, by the detecting unit, whether the shorting bar circuit in the panel is cut off based on the detecting image.

* * * * *